(12) United States Patent
Kaneko et al.

(10) Patent No.: US 7,683,222 B2
(45) Date of Patent: Mar. 23, 2010

(54) METHOD OF PRODUCING A FLUORINE-CONTAINING COMPOUND

(75) Inventors: Yushi Kaneko, Minami-ashigara (JP); Takayuki Ito, Minami-ashigara (JP); Taizo Ono, Nagoya (JP)

(73) Assignee: Fujifilm Corporation, Tokyo (JP)

( * ) Notice: Subject to any disclaimer, the term of this patent is extended or adjusted under 35 U.S.C. 154(b) by 1059 days.

(21) Appl. No.: 11/242,776

(22) Filed: Oct. 5, 2005

(65) Prior Publication Data

US 2006/0074260 A1 Apr. 6, 2006

(30) Foreign Application Priority Data

Oct. 6, 2004 (JP) .............................. 2004-294231

(51) Int. Cl.
*C07C 17/00* (2006.01)

(52) U.S. Cl. ...................................... 570/161

(58) Field of Classification Search ................. 570/127, 570/161
See application file for complete search history.

(56) References Cited

U.S. PATENT DOCUMENTS 5,322,904 A * 6/1994 Bierschenk et al. ...... 525/331.6
5,399,718 A 3/1995 Costello et al.

FOREIGN PATENT DOCUMENTS

WO WO-00/56694 A1 9/2000

\* cited by examiner

*Primary Examiner*—Jafar Parsa
(74) *Attorney, Agent, or Firm*—Birch, Stewart, Kolasch & Birch, LLP

(57) ABSTRACT

A method of producing a fluorine-containing compound, which contains the step of: fluorinating a substrate in a solvent with fluorine gas, wherein as said substrate, a substrate that cannot substantially undergo fluorinating reaction independently, is allowed to react, in the presence of a substrate that rapidly undergoes fluorinating reaction independently.

8 Claims, No Drawings

METHOD OF PRODUCING A FLUORINE-CONTAINING COMPOUND

FIELD OF THE INVENTION

The present invention relates to a method of producing a fluorine-containing compound.

BACKGROUND OF THE INVENTION

Perfluoro compounds are excellent in chemical stability, dielectric constant lowness, refractive index lowness, viscosity lowness, lubricity, water repellency and oil repellency, non-adhesiveness, and the like, and they are applied to various materials, such as fluorocarbon rubbers, materials for plenum cables, optical fibers, antireflective films, pellicles, and the like. In recent years, therefore, methods of synthesizing a perfluoro compound effectively have actively been developed.

One method of synthesizing a perfluoro compound effectively is a direct fluorination method using fluorine gas. This method is very attractive from the viewpoint of energy-saving and high selectivity of a product, since, for example, this method is different from electrolytic fluorination, which requires vast energy and may generate a compound composed of mixed isomers. However, the direct fluorination method has a problem that the following occasionally advance: cleavage of carbon-carbon chains, oligomerization, generation of high heat, and explosive reaction.

Known methods of solving such a problem are to inject a substrate into an inert solvent, together with an excessive amount of fluorine (see, for example, U.S. Pat. Nos. 5,322,904 and 5,399,718, and International Publication No. WO 00/56694 pamphlet). In this method, fluorine is saturated into a solvent inert to fluorine, which will be referred to as an inert solvent hereinafter, and examples thereof include flon-series solvents and perfluoro alkane-series solvents. A substrate and fluorine are then introduced into the inert solvent such that the amount of fluorine would be excessive, i.e. the mol number of fluorine is not less than the amount necessary to fluorinate the substrate completely, thereby restraining coupling reaction between molecules of the substrate, decomposition reaction of the substrate, and explosive reaction. However, if the substrate accumulates in a reaction container without being effectively fluorinated and the reaction proceeds all at once at some point of time, it is expected that there is risk due to much heat generation and explosion is possible.

To avoid such risk, it is indispensable to cause the fluorination to proceed effectively from the early stage of the reaction. For this purpose, it is necessary to set conditions for causing the substrate to react effectively with fluorine.

One condition for causing the substrate to react effectively with fluorine is that "the substrate is soluble in a solvent and has a bond that reacts easily with fluorine." Of inert solvents, flon-series solvents are excellent in dissolving power. Thus, fluorinating reaction using a flon solvent is known (see, for example, U.S. Pat. Nos. 5,322,904 and 5,399,718). However, flon-series solvents have the problems that they are not easily available and that they are environmentally harmful compounds that deplete the ozone layer. Consequently, it would be difficult to use the flon-series solvents for the production of a perfluoro compound. Further, even in the case of using a flon-series solvent, there is the problem of explosion, depending on a structure of the substrate to be used (see, for example, Journal of Synthetic Organic Chemistry, Japan, 2003, vol. 61, No. 2, p. 164).

In another known example, a solvent other than flon-series solvents, such as Fluorinert FC-72 (trade name, manufactured by 3M Co.), is used to conduct fluorination (see, for example, U.S. Pat. No. 5,399,718). This solvent is inferior to flon-series solvents in power for dissolving hydrocarbon compounds. When this solvent is used to perform fluorination, the reaction proceeds as in the example described in U.S. Pat. No. 5,399,718, if a substrate may be dissolved in the solvent even in a small amount thereof, and the substrate has a bond that reacts easily with fluorine. However, if the substrate is hardly dissolved in the solvent, and further the substrate has a bond that does not react easily with fluorine, it is observed that the reaction thereof does not proceed at all, and the substrate floats in the reaction system.

When the solubility of a substrate in inert solvent is poor, another known method is to perform fluorination using a compound in which fluorine is partially introduced into the substrate in advance (see, for example, International Publication No. WO 00/56694 pamphlet, and Journal of Synthetic Organic Chemistry, Japan, 2003, vol. 61, No. 2, p. 164). However, in this case, the substrate is restricted to a substrate into which fluorine can be introduced in advance, thereby causing a problem that the range of compounds that can be fluorinated becomes narrow. Further, there is caused a problem that the cost for the substrate's raw material increases, since fluorine is beforehand introduced into the material.

SUMMARY OF THE INVENTION

The present invention resides in a method of producing a fluorine-containing compound, which comprises the step of:
fluorinating a substrate in a solvent with fluorine gas, wherein as said substrate, a substrate that cannot substantially undergo fluorinating reaction independently, is allowed to react, in the presence of a substrate that rapidly undergoes fluorinating reaction independently.

Other and further features and advantages of the invention will appear more fully from the following description.

DETAILED DESCRIPTION OF THE INVENTION

According to the present invention, there is provided the following means:
(1) A method of producing a fluorine-containing compound, comprising the step of:
fluorinating a substrate in a solvent with fluorine gas, wherein as said substrate, a substrate that cannot substantially undergo fluorinating reaction independently, is allowed to react, in the presence of a substrate that rapidly undergoes fluorinating reaction independently.
(2) The method of producing a fluorine-containing compound according to item (1), wherein the substrate that cannot substantially undergo fluorinating reaction independently is to cause phase separation with the solvent.
(3) The method of producing a fluorine-containing compound according to item (1) or (2), wherein the substrate that cannot substantially undergo fluorinating reaction independently has a fluorine content of 30 mass % or less.
(4) The method of producing a fluorine-containing compound according to any one of items (1) to (3), wherein the substrate that cannot substantially undergo fluorinating reaction independently has at least one electron-withdrawing group.
(5) The method of producing a fluorine-containing compound according to any one of items (1) to (4), wherein the solvent is a solvent that does not cause depletion of any ozone layer and does not substantially react with fluorine.
(6) The method of producing a fluorine-containing compound according to any one of items (1) to (5), wherein the solvent comprises at least one solvent selected from perfluoro alkanes, perfluoro cycloalkanes, perfluoro ethers, perfluoro alkylamines, and perfluoro acyl fluorides.
(7) The method of producing a fluorine-containing compound according to any one of items (1) to (6), wherein the substrate that rapidly undergoes fluorinating reaction independently is soluble to the solvent.

The present invention and the best mode for carrying out the invention are described in detail below.

The fluorination according to the present invention, which is carried out in the presence (or coexistence) of a substrate that rapidly undergoes fluorinating reaction independently, is very effective to the case in which ordinary fluorination, which is carried out in the absence of any substrate that rapidly undergoes fluorinating reaction independently, does not proceed at all or does proceed slowly. Further, even in the case in which the ordinary fluorination proceeds, the reaction may be progressed more safely and effectively, by applying the fluorination method according to the present invention. In the present invention, the substrate is a compound having a C—H bond or/and a carbon-carbon unsaturated bond, which may be in any form of solid, liquid or gas. The substrate is preferably in the form of liquid. The substrate may or may not contain a C—F bond in advance. The term "substrate that rapidly undergoes fluorinating reaction independently" means a compound that, in a reaction of said substrate (one kind only) and fluorine gas in an amount not less than the theoretical equivalent to perfluorination of the substrate, are simultaneously and continuously added into a solvent (this reaction will be discussed in detail below), the perfluorination of the substrate substantially completes when the addition of the substrate is finished. Herein, the term "perfluorination" means that fluorine gas is added to all carbon-carbon unsaturated bonds in the substrate until each bond is saturated, and further all of the C—H bonds are converted to C—F bonds. The term "perfluorination of the substrate substantially completes when the addition of the substrate is finished" means that the fluorine gas is consumed in the fluorination of the substrate in an amount of 90% or more, to the fluorine gas amount necessary for the perfluorination of the substrate. In other words, the term means that 90% or more by number of all sites of the substrate which can be fluorinated are fluorinated. Further, the term "substrate that cannot substantially undergo fluorinating reaction independently" means a compound that perfluorination of the substrate does not complete when the addition of the substrate is finished in the above-mentioned reaction. The term "perfluorination of the substrate does not complete when the addition of the substrate is finished" means that the amount of the fluorine gas consumed actually for the fluorination of the substrate is 50% or less, to the fluorine gas amount necessary for the perfluorination of the substrate.

The substrate that cannot substantially undergo fluorinating reaction independently will be described further in detail below. It is very difficult to specify the substrate that cannot substantially undergo fluorinating reaction independently, by defining said substrate with its structure, some physical property thereof, or the like. Accordingly, whether a compound in interest is a substrate that cannot substantially undergo fluorinating reaction independently, or not, can only be identified from a result obtained by actually conducting ordinary fluorinating reaction of said compound in interest. In this connection, however, one property that a substrate that cannot substantially undergo fluorinating reaction independently may possibly have is, for example, that said substrate causes phase separation with a solvent. The substrate that causes phase separation with a solvent may be selected from a wide range of compounds depending on the structure, composition or physical property of solvent, or reaction conditions (e.g. temperature), and it cannot generally be defined, but it is a compound having a fluorine content of 30 mass % or less, in many cases. Herein, the term "phase separation" means that when a compound in interest is added to a solvent in an amount identical to the mass of said solvent to mix these, the resultant system is to be a heterogeneous system. When a reaction is to be proceeded in a heterogeneous system, as described, for example, in International Publication No. WO 00/56694 pamphlet, there may be disadvantage to the reaction in many cases. However, according to the method of the present invention, it is possible to progress the reaction with no problem even in a heterogeneous system. Further, since a fluorine atom high in electronegativity is associated in fluorination, it may occur with a high possibility that the fluorination reaction rate be slow, if a reaction site in a substrate to be used has an electron-withdrawing group. Examples of the electron-withdrawing group include a fluorine atom, a chlorine atom, a bromine atom, an iodine atom, a nitro group, a sulfonylfluoride group, a sulfonylchloride group, and an acid amido group. Of these, when a chlorine atom is possessed at a reaction site, fluorination reaction progresses slowly, in many cases.

The substrate that cannot substantially undergo fluorinating reaction independently and the substrate that rapidly undergoes fluorinating reaction independently may be introduced separately, or in the form of a mixture of these. These substrates each may be introduced, with being dissolved (or dispersed) in a solvent. The above two substrate are preferably introduced in the form of a mixture thereof without using any solvent. In this case, the two are more preferably in a homogeneous mixture form.

The amount to be used of the substrate that rapidly undergoes fluorinating reaction independently is preferably 0.005 to 2 times, more preferably 0.01 to 1 time, and further preferably 0.05 to 0.5 time, as large as that of the substrate that cannot substantially undergo fluorinating reaction independently (i.e. the substrate that undergoes fluorinating reaction slowly), in terms of the fluorine gas amount necessary for perfluorination.

The solvent that can be used in the present invention is preferably a solvent that does not cause any depletion of the ozone layer, and that substantially does not react with fluorine. Herein, the term "solvent substantially does not react with fluorine" means that when fluorine gas is introduced in the solvent, the amount of said fluorine gas used for reaction with the solvent is 10 mol % or less, in the total amount of the introduced fluorine gas. Examples of the solvent include perfluoro alkanes (which may be a mixture composed of structural isomers, e.g. perfluoropentane, perfluorohexane, perfluoroheptane, and perfluorooctane), perfluoro cycloalkanes (which may be a mixture composed of structural isomers, e.g. perfluorocyclopentane, perfluorocyclohexane, perfluorocycloheptane, and perfluorocyclooctane), perfluoro ethers (which may be a mixture composed of structural isomers, e.g. Fluorinert™ FC-75 (trade name, manufactured by 3M Co.), and Krytox™ (trade name, manufactured by Du Pont Co.)), perfluoro alkylamines (which may be a mixture composed of structural isomers, e.g. perfluorotributylamine), perfluoro acyl fluorides (which may be a mixture composed of structural isomers, e.g. perfluoro(2-methyl-3-oxahexanoyl) fluoride, perfluoro(2,5,8-trimethyl-3,6,9-trioxadodecanoyl) fluoride), hydrogen fluoride, water, trifluoroacetic acid, and supercritical carbon dioxide. Of the above-mentioned solvents, use can be made, in some cases, of solvents partially having sites where the solvents can react with fluorine; and examples thereof include those in which fluorine atoms are partially substituted by hydrogen atoms (e.g. 6H-tridecafluorohexane, 2,2-bis(trifluoromethyl)propionyl fluoride), and those in which fluorine atoms are partially substituted by halogen atoms (e.g. perfluorooctyl iodide, perfluorohexyl bromide). These solvents may be used singly, or in combination of two or more of these. Of the above-mentioned solvents, a perfluoro alkane, a perfluoro cycloalkane, a perfluoro ether, a perfluoro alkylamine, and a perfluoro acyl fluoride are most preferred; The amount of the solvent to be used is preferably 0.1 to 500 times, more preferably 1 to 300 times, and further preferably 3 to 200 times, as large as the volume of the substrate to be injected.

The substrate that rapidly undergoes fluorinating reaction independently, in the above solvent, means a compound having at least one, preferably two or more or a plurality of site(s) at which reaction with fluorine can proceed. Examples thereof include a linear, branched or cyclic hydrocarbon compound having 5 to 30 carbon atoms, which may contain a fluorine atom, an oxygen atom, or/and an unsaturated bond, provided that the hydrocarbon compound has at least one unsaturated bond or at least one C—H bond in the molecule. Specific examples thereof include pentane, hexane, hexene, cyclohexane, cyclohexene, diethyl ether, tetrahydrofuran, ethyl acetate, hexafluoroisopropyl methyl ether, 1,1,2,3,3,3-hexafluoropropyl ethyl ether, benzene, toluene, fluorobenzene, trifluoromethylbenzene, 4-fluorotrimethylbenzene, and hexafluorobenzene. The above compounds, which may be soluble or insoluble in a solvent to be used, can be used in the present invention, without particular limitation, as long as they can accelerate the reaction, but it is preferable that the compound is soluble in the solvent (generally, a solubility of said compound in said solvent is 1 g/100 ml or more at 25° C.).

In the reaction according to the present invention, the fluorine gas may be used, as it is, without being diluted. For safety, the fluorine gas is preferably used in the state of mixed gas with an inert gas. The inert gas is preferably nitrogen gas or helium gas. From the viewpoint of economy, nitrogen gas is preferred. The concentration of the fluorine gas in the inert gas is preferably from 10 to 50% by volume, more preferably from 20 to 30% by volume.

In the reaction according to the present invention, a substrate that cannot substantially undergo fluorinating reaction independently and a substrate that rapidly undergoes fluorinating reaction independently are introduced into a solvent, together with a fluorine gas. For this introduction, the fluorine gas amount is preferably kept to be 1 to 2 times, more preferably 1.2 to 1.5 times, as large as the fluorine gas amount necessary for the perfluorination of both the substrate that cannot substantially undergo fluorinating reaction independently and the substrate that rapidly undergoes fluorinating reaction independently. The reaction temperature in this case is preferably from −50 to 100° C., more preferably from −20 to 50° C., and further preferably from −10 to 30° C.

When the reaction is conducted under the conditions as described above, the perfluorination of the substrate may substantially complete immediately after the addition of the substrate, in the case of a specific substrate. Alternatively, a large amount of a hydrogen-containing intermediate product may remain. In the latter case, the progress of the reaction is very slow only by continuing to blow the fluorine gas in the reaction system. To rapidly finish fluorination completely, it is necessary to perform an operation of adding the fluorine gas together with a reaction accelerating agent for a period of time. The reaction accelerating agent may be the above-mentioned substrate that rapidly undergoes fluorinating reaction independently. The amount of the reaction accelerating agent to be used is preferably adjusted such that the total number of sites that can be fluorinated in the reaction accelerating agent would be preferably 0.1 to 20%, more preferably 0.2 to 5%, to the total number of sites that can be fluorinated in the substrate. The reaction accelerating agent is preferably added in the state that the fluorine gas is present. With respect to the addition method thereof, it is possible to add the accelerating agent followed by injecting fluorine under pressure, or to add the accelerating agent and the fluorine gas simultaneously similar to the addition of the substrate.

In the reaction according to the present invention, when reaction for substituting a hydrogen atom(s) in the substrate by a fluorine atom(s) progresses, hydrogen fluoride is produced as a byproduct. The thus-produced hydrogen fluoride can be trapped, by providing a hydrogen fluoride-scavenger to be coexistent in the reaction system, or by filling the hydrogen fluoride-scavenger in a line for a discharge gas. The hydrogen fluoride-scavenger is preferably an alkali metal fluoride, such as sodium fluoride or potassium fluoride, and is particularly preferably sodium fluoride.

According to the present invention, there can be provided a novel method of producing a perfluoro compound, in which fluorination can be effectively conducted in a readily available solvent.

The method of producing a fluorine-containing compound according to the present invention is a highly effective production method, which is energy saving and excellent in selectivity of a product, and which can effectively proceed fluorination from the initial stage of the reaction. Accordingly, the method of the present invention is excellent in safety, since the method does not have such risk of explosion or high heat generation.

Further, in the method of the present invention, the solvent to be used is readily available, since the solvent is a solvent other than flon-series solvents. It is also unnecessary to introduce fluorine partially into a substrate in advance. Accordingly, a fluorine-containing compound can be produced at low costs. In particular, a substrate that cannot substantially undergo fluorinating reaction independently can be effectively fluorinated.

The present invention will be described in more detail based on the following example, but the invention is not intended to be limited thereto.

EXAMPLE

Example 1

Synthesis of Perfluoro Compound B by Fluorinating Compound A

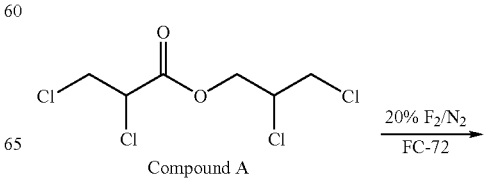

Compound A

-continued

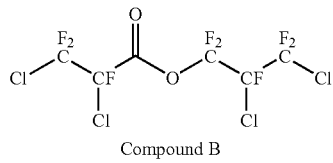

Compound B

A solvent (FC-72, trade name, manufactured by 3M Co.) (175 mL) was charged into a 250-mL reaction vessel made of Teflon (trade name, tetrafluoroethylene), and this system was kept at −10° C. A NaF pellet filled layer and a condenser kept at −40° C. were connected in series to an outlet of the reaction vessel, such that the liquid condensed with the condenser would be returned to the reaction vessel through a returning line. Helium gas was blown into the vessel at a rate of 20 mL/min for 30 minutes. Thereafter, fluorine gas diluted into 20% with nitrogen gas, which will be simply referred to as "fluorine gas" hereinafter, was blown into the vessel at a rate of 100 mL/min for 1 hour. While the fluorine gas was blown into the vessel at the same rate, a hydrocarbon compound A (4.25 mmol, 1.08 g) and hexane (0.243 mmol, 0.020 g) were injected thereinto over 63 minutes. At this point of time, the presence of a target compound, perfluoro body B, and a hydrogen-remaining body, in which fluorination was not completely conducted, was observed by gas chromatography measurement. Thereafter, a solution (10 mL) in which hexafluorobenzene (1.72 mmol, 0.32 g) was dissolved in the solvent (FC-72) was injected into the vessel over 2 hours, and then the resultant was again analyzed by gas chromatography. As a result, only a peak of the target compound B was observed. The flow of the fluorine gas was stopped, and helium gas was blown thereinto at a rate of 20 mL/min for 1 hour. Thereafter, the solvent was concentrated, and the resultant was distilled, to yield the compound B at yield 35%.

Comparative Example 1

The reaction was tried to proceed under the same conditions as in Example 1, except that hexane and hexafluorobenzene were not added. As a result, no reaction proceeded at all, and an oil composed of organic substances floated on the solvent. This oil was analyzed by gas chromatography. As a result, it was found out that the starting compound A was contained in an amount of 91.7 GLC area percentages.

Results

As is apparent from the results of Example 1 and Comparative Example 1, according to the present invention, the compound A, which cannot substantially undergo fluorinating reaction independently, can be effectively fluorinated.

Having described our invention as related to the present embodiments, it is our intention that the invention not be limited by any of the details of the description, unless otherwise specified, but rather be construed broadly within its spirit and scope as set out in the accompanying claims.

What we claim is:

1. A method of producing a fluorine-containing compound, comprising the step of: fluorinating a first substrate in a solvent with fluorine gas, wherein said first substrate is a substrate that cannot substantially undergo fluorinating reaction independently, and is allowed to react in the presence of a second substrate that rapidly undergoes fluorinating reaction independently, and wherein the substrate that cannot substantially undergo fluorinating reaction independently causes phase separation with the solvent.

2. The method of producing a fluorine-containing compound according to claim 1, wherein the substrate that cannot substantially undergo fluorinating reaction independently has a fluorine content of 30 mass % or less.

3. The method of producing a fluorine-containing compound according to claim 1, wherein the substrate that cannot substantially undergo fluorinating reaction independently has at least one electron-withdrawing group.

4. The method of producing a fluorine-containing compound according to claim 1, wherein the solvent is a solvent that does not cause depletion of any ozone layer and does not substantially react with fluorine.

5. The method of producing a fluorine-containing compound according to claim 1, wherein the solvent comprises at least one solvent selected from the group consisting of perfluoro alkanes, perfluoro cycloalkanes, perfluoro ethers, perfluoro alkylamines, and perfluoro acyl fluorides.

6. The method of producing a fluorine-containing compound according to claim 1, wherein the substrate that rapidly undergoes fluorinating reaction independently is soluble in the solvent.

7. The method of producing a fluorine-containing compound according to claim 1, further comprising the step of:

conducting further fluorination reaction by adding a fluorine gas and a reaction accelerating agent, after the first fluorinating step, wherein said reaction accelerating agent is an additional second substrate.

8. The method of producing a fluorine-containing compound according to claim 1, wherein the substrate that rapidly undergoes fluorinating reaction independently is a linear, branched or cyclic hydrocarbon compound having 5 to 30 carbon atoms, optionally containing at least one selected from the group consisting of a fluorine atom, an oxygen atom, and an unsaturated bond, and having at least one unsaturated bond or C—H bond.

* * * * *